(12) United States Patent
Diab

(10) Patent No.: US 7,801,581 B2
(45) Date of Patent: *Sep. 21, 2010

(54) OPTICAL SPECTROSCOPY PATHLENGTH MEASUREMENT SYSTEM

(75) Inventor: Mohamed K. Diab, Mission Viejo, CA (US)

(73) Assignee: Masimo Laboratories, Inc., Irvine, CA (US)

( * ) Notice: Subject to any disclaimer, the term of this patent is extended or adjusted under 35 U.S.C. 154(b) by 911 days.

This patent is subject to a terminal disclaimer.

(21) Appl. No.: 11/636,863

(22) Filed: Dec. 11, 2006

(65) Prior Publication Data

US 2007/0083093 A1 Apr. 12, 2007

Related U.S. Application Data

(63) Continuation of application No. 10/695,405, filed on Oct. 28, 2003, now Pat. No. 7,149,561, which is a continuation of application No. 09/925,982, filed on Aug. 9, 2001, now Pat. No. 6,640,116.

(60) Provisional application No. 60/226,428, filed on Aug. 18, 2000.

(51) Int. Cl.
*A61B 5/1455* (2006.01)

(52) U.S. Cl. .................. 600/310; 600/322; 356/367

(58) Field of Classification Search .............. 600/310, 600/316, 322, 323, 336; 356/364, 365, 366, 356/367, 368

See application file for complete search history.

(56) References Cited

U.S. PATENT DOCUMENTS 4,960,128 A 10/1990 Gordon et al.

(Continued)

FOREIGN PATENT DOCUMENTS

WO WO 9809566 3/1998

OTHER PUBLICATIONS

Browne A F et al., "Microdegree Polarimetric Measurement of Glucose Concentrations for Biotechnology Applications", Proceedings of the IEEE 23$^{rd}$, Northeast Bioengineering Conference, Durham, New Hampshire, May 21-22, 1997, Proceedings of the IEEE Northeast Bioengineering Conference, New York, IEEE, US, vol. Conf. 23, May 21, 1997, pp. 9-10, XP000738103, ISBN:0-7803-3849-9.

(Continued)

*Primary Examiner*—Eric F Winakur
(74) *Attorney, Agent, or Firm*—Knobbe Martens Olson & Bear LLP

(57) ABSTRACT

A physiological monitor utilizes rotation measurements to estimate mean photon pathlengths through tissue. These pathlength estimates, along with corresponding optical spectroscopy measurements allow the noninvasive monitoring of blood constituent concentrations. The technique is particularly applicable to noninvasive blood glucose measurements. The physiological monitor has a polarized light source for illuminating tissue and a magnetic field generator which creates a magnetic field within the tissue during illumination. The magnetic field imparts a rotation in the plane of polarization of the incident light beam as it propagates through the tissue and emerges as a transmitted light beam. A polarimeter is used to measure the rotation of the transmitted light. A signal processor then computes an estimate of the mean pathlength from the polarimeter output. The polarized light source has a multiple wavelength optical emitter and, in conjunction with the polarimeter detector, also functions as a spectrometer. The signal processor combines spectroscopic measurements at various wavelengths with corresponding mean pathlength estimates to compute blood constituent concentrations.

18 Claims, 17 Drawing Sheets

U.S. PATENT DOCUMENTS

| | | | |
|---|---|---|---|
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,337,744 A | 8/1994 | Branigan |
| D353,195 S | 12/1994 | Savage et al. |
| D353,196 S | 12/1994 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,871,442 A | 2/1999 | Madarasz et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,064,898 A | 5/2000 | Aldrich |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,166,807 A | 12/2000 | Kawamura et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 * | 10/2003 | Diab ........................ 600/322 |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Diab et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,585 B1 | 4/2004 | Parker |
| 6,725,075 B2 | 4/2004 | Al-Ali |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |

| | | |
|---|---|---|
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Al et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |

OTHER PUBLICATIONS

Jang Sunghoon and Fox Martin D, "Double Lock-in Concept for More Glucose Detection", Proceedings of the IEEE 25$^{th}$ Annual Northeast Bioengineering Conference, West Hartfore, CT, Apr. 8-9, 1999, Proceedings of the IEE Annual Northeast Bioengineering Conference, New York, Ny, pp. 122-124, XP002155401, ISBN: 1-7803-5487-7.

T.R. Nelson and Dr. Robert B. Northrop, "Optical Glucose Measurement Using a Microdegree Polarimeter in a Closed Loop System", published electronically Jul. 30, 1998, 15 pages.

International Search Report, PCT Article 18, 1-4 pages, Filing Date Aug. 14, 2001.

Notification of Transmittal of the International Search Report or the Declaration, 1-3 pages, date of mailing Mar. 18, 2002.

* cited by examiner

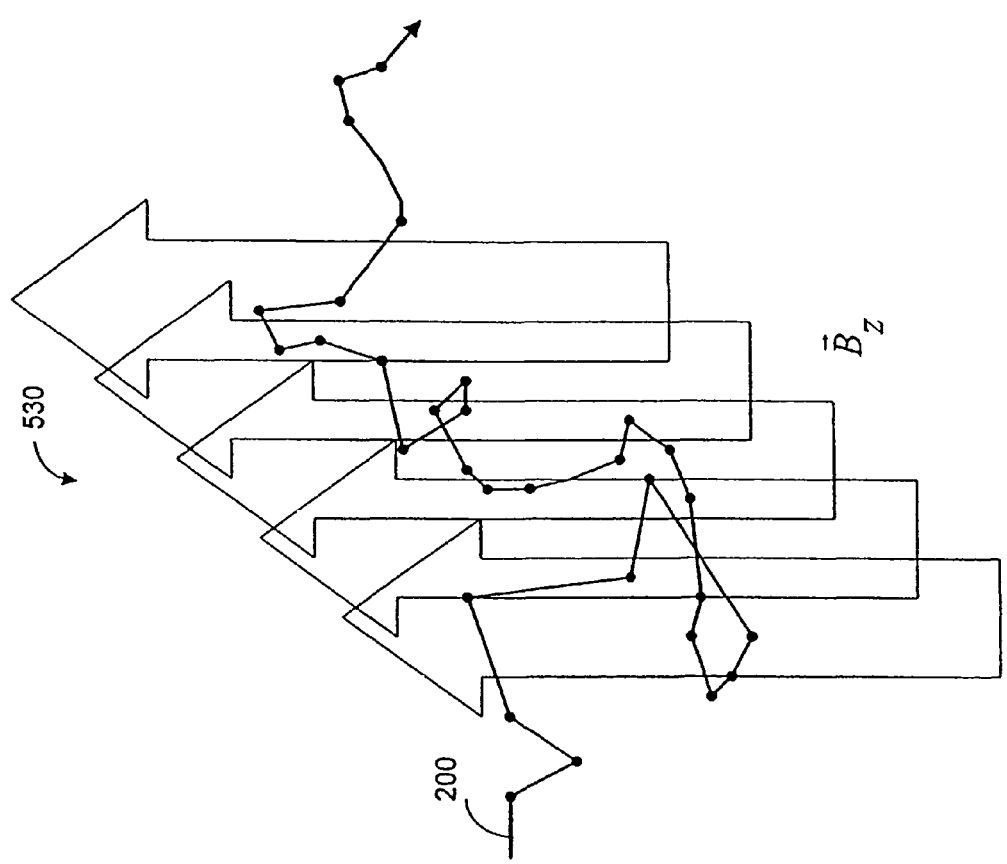

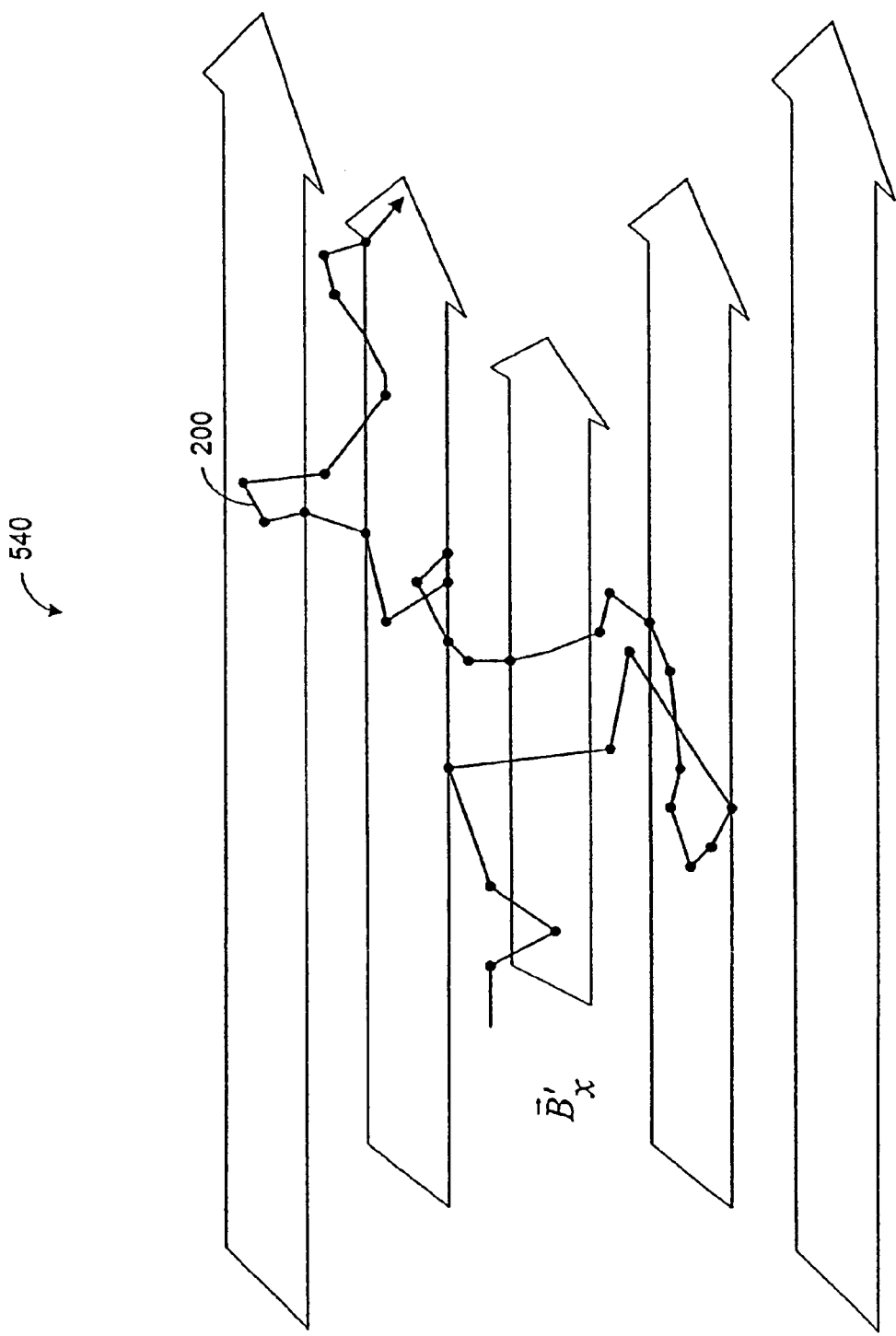

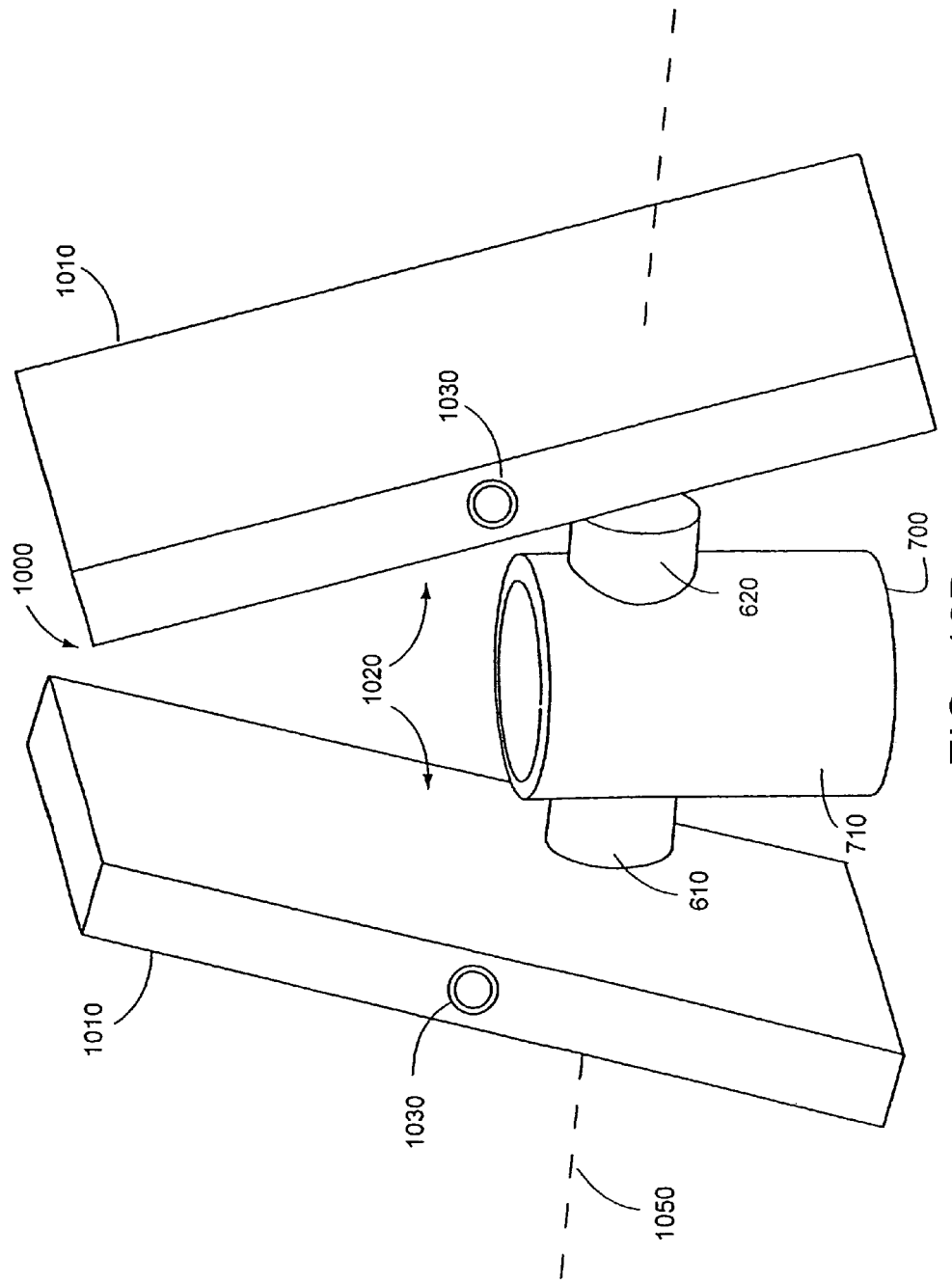

OPTICAL SPECTROSCOPY PATHLENGTH MEASUREMENT SYSTEM

REFERENCE TO PRIOR APPLICATIONS

This application is a continuation of U.S. patent application Ser. No. 10/695,405 filed, Oct. 28, 2003 now U.S. Pat. No. 7,149,561, entitled "Optical Spectroscopy Pathlength Measurement System," which is a continuation of U.S. patent application Ser. No. 09/925,982, filed Aug. 9, 2001, now U.S. Pat. No. 6,640,116, entitled "Optical Spectroscopy Pathlength Measurement System," which claims a priority benefit under 35 U.S.C. §119(e) from U.S. Provisional Patent Application No. 60/226,428, filed on Aug. 18, 2000. The present application incorporates each of the foregoing disclosures herein by reference.

BACKGROUND OF THE INVENTION

Various optical spectroscopic measurement systems have been developed for the noninvasive monitoring of blood constituents. In such systems, light of multiple wavelengths is used to illuminate a thin tissue portion of a person, such as a fingertip or earlobe, to obtain a spectrum analysis of the light absorbed by blood flowing through the tissue site. Pulse oximetry systems, which perform such measurements to monitor blood oxygenation of hemoglobin constituents, have been particularly successful in becoming the standard of care. Extending this technology to the noninvasive monitoring of other blood constituents, such as blood glucose, is highly desirable. For example, current methods for accurately measuring blood glucose involve drawing blood from the subject, which can be onerous for diabetics who must take frequent samples to closely monitor blood glucose levels.

FIG. 1 illustrates an optical spectroscopic measurement system 100. A multiple wavelength light source 110 produces incident light 112 of intensity $I_0$ and wavelength $\lambda$, $I_{0,\lambda}$, which illuminates a sample 120 having multiple constituents, each of concentration $c_i$. The incident light 112 is partially absorbed by the sample 120, and transmitted light 130 of intensity I emerges from the sample 120. A detector 140 provides an output signal 142 that is proportional to the transmitted light 130. A signal processor 150 operates on the detector output signal 142 to provide a measurement 152 that is indicative of one or more of the constituent concentrations $c_i$ in the sample 120, based upon the known extinction coefficients $\epsilon_{i,\lambda}$ of the sample constituents.

SUMMARY OF THE INVENTION

The attenuation of light through a homogenous, non-scattering medium of thickness d having n dissolved, absorbing constituents is described by the Beer-Lambert Law $$I = I_{0,\lambda} e^{-\sum_{i=1}^{n} \varepsilon_{i,\lambda} \cdot c_i \cdot d} \tag{1}$$

Dividing both sides by $I_{0,\lambda}$ and taking the logarithm yields $$\ln(I/I_0) = -\mu_a \cdot d \tag{2a}$$

$$\mu_a = \sum_{i=1}^{n} \varepsilon_{i,\lambda} \cdot c_i \tag{2b}$$

where $\mu_a$ is the bulk absorption coefficient and represents the probability of absorption per unit length. Measurements are taken at n wavelengths to yield n equations in n unknowns $$\begin{bmatrix} \ln(I_{\lambda_1}/I_{0,\lambda_1}) \\ \ln(I_{\lambda_2}/I_{0,\lambda_2}) \\ \vdots \\ \ln(I_{\lambda_n}/I_{0,\lambda_n}) \end{bmatrix} = - \begin{bmatrix} \varepsilon_{1,\lambda_1} & \varepsilon_{2,\lambda_1} & \cdots & \varepsilon_{n,\lambda_1} \\ \varepsilon_{1,\lambda_2} & \varepsilon_{2,\lambda_2} & \cdots & \varepsilon_{n,\lambda_2} \\ \vdots & \vdots & \ddots & \vdots \\ \varepsilon_{1,\lambda_n} & \varepsilon_{2,\lambda_n} & \cdots & \varepsilon_{n,\lambda_n} \end{bmatrix} \begin{bmatrix} c_1 \\ c_2 \\ \vdots \\ c_n \end{bmatrix} d \tag{3}$$

which can be written in matrix notation as $$I = -\mathbf{A}(\lambda) C d \tag{4}$$

Solving for the constituent concentrations yields $$C = -\frac{1}{d} \mathbf{A}(\lambda)^{-1} I \tag{5}$$

If the medium is a tissue portion of a person, such as a fingertip, it includes a number of constituents that absorb light. Some of the principal absorbing constituents in tissue include water, oxyhemoglobin, reduced hemoglobin, lipids, melanin and bilirubin. A drawback to applying the Beer-Lambert Law to determine the concentrations of absorbing constituents, however, is that tissue is a turbid media, i.e. strongly scatters light, which violates an underlying assumption of equation (1). Scattering in tissue is due, in part, to the variations in refractive index at the boundaries of cells or other enclosed particles, such as collagen fibers, mitochondria, ribosomes, fat globules, glycogen and secretory globules.

FIG. 2 illustrates a particular photon path 200 as it travels through a turbid medium 202. The photon path 200 is shown as a series of connected vectors $\vec{p}\,l_i$ each representing the direction and pathlength of a particular photon between collisions. The total pathlength traveled by the photon is $$pl = \sum_{i=1}^{n} \sqrt{pl_{ix}^2 + pl_{iy}^2 + pl_{iz}^2} \tag{6}$$

As shown in FIG. 2, the effect of scattering is to substantially increase the photon pathlength and, hence, the probability of absorption. Thus, when a turbid media is considered, the Beer-Lambert Law is modified to include the effective pathlength, pl, which is a function of wavelength. The Beer-Lambert Law is also written in terms of transmission, T, to differentiate reflected light due to back-scattering of the incident light.

$$T = T_{max} e^{-\sum_{i=1}^{n} \varepsilon_{i,\lambda} \cdot c_i \cdot pl_\lambda} \tag{7}$$

where $T_{max}$ is the maximum transmitted light without absorption.

$$\begin{bmatrix} \ln(T_{\lambda_1}/T_{max,\lambda_1}) \\ \ln(T_{\lambda_2}/T_{max,\lambda_2}) \\ \vdots \\ \ln(T_{\lambda_n}/T_{max,\lambda_n}) \end{bmatrix} = -\begin{bmatrix} pl_{\lambda_1} & 0 & 0 & 0 \\ 0 & pl_{\lambda_2} & 0 & 0 \\ 0 & 0 & \ddots & 0 \\ 0 & 0 & 0 & pl_{\lambda_n} \end{bmatrix} \quad (8)$$

$$\begin{bmatrix} \varepsilon_{1,\lambda_1} & \varepsilon_{2,\lambda_1} & \cdots & \varepsilon_{n,\lambda_1} \\ \varepsilon_{1,\lambda_2} & \varepsilon_{2,\lambda_2} & \cdots & \varepsilon_{n,\lambda_2} \\ \vdots & \vdots & \ddots & \vdots \\ \varepsilon_{1,\lambda_n} & \varepsilon_{2,\lambda_n} & \cdots & \varepsilon_{n,\lambda_n} \end{bmatrix}\begin{bmatrix} c_1 \\ c_2 \\ \vdots \\ c_n \end{bmatrix}$$

$$T = -X(\lambda)\mathbf{A}(\lambda)C \quad (9)$$

$$C = -\mathbf{A}(\lambda)^{-1}X(\lambda)^{-1}T \quad (10)$$

FIG. 3 illustrates one method of measuring the effective pathlength through a sample. A picosecond pulse laser 310 and an ultra-fast detector 340 directly measure the photon "time of flight" through a sample 320. A single pulse 360 with a duration on the order of a picosecond is directed through the sample 320. The detector 340 measures the corresponding impulse response 370. The time difference between the light entering the sample 312 and the mean time of flight, $\bar{t}$ 380, of light having traversed the sample 330 yields the mean optical pathlength, i.e. the effective pathlength $$mpl = c_v \bar{t}/n_s \quad (11a)$$

$$\bar{t} = \int_0^\infty T(t)t\, dt \Big/ \int_0^\infty T(t)\, dt \quad (11b)$$

where $c_v$ is the speed of light in a vacuum and $n_s$ is the refractive index of the sample. An analytic expression for the shape of the impulse response of a narrow collimated pulsed light beam normally incident on the surface of a semi-infinite homogeneous tissue slab of thickness d, derived from the diffusion approximation to radiative transfer theory, is $$T(d,t) = (4\pi Dc)^{-1/2} t^{-3/2} e^{-\mu_a ct} f(t) \quad (12a)$$

$$f(t) = \left\{ (d-z_0)e^{-\left[\frac{(d-z_0)^2}{4Dct}\right]} - (d+z_0)e^{-\left[\frac{(d+z_0)^2}{4Dct}\right]} + \right. \quad (12b)$$

$$\left. (3d-z_0)e^{-\left[\frac{(3d-z_0)^2}{4Dct}\right]} - (3d+z_0)e^{-\left[\frac{(3d+z_0)^2}{4Dct}\right]} \right\}$$

$$D = \{3[\mu_a + (1-g)\mu_s]\}^{-1} \quad (12c)$$

$$z_0 = [(1-g)\mu_s]^{-1} \quad (12d)$$

where T(d, t) is the spatially integrated transmittance, D is the diffusion coefficient, c is the speed of light in the tissue, $\mu_a$ is the bulk absorption coefficient, $\mu_s$ is the bulk scattering coefficient and g is the anisotropy, which is the mean cosine of the scattering angle. Equations (12a)-(12d), therefore, are an approximation of the impulse response 370 shown in FIG. 3. The derivation of equations (12a)-(12d) and a description of the model upon which that derivation is based, is given in *Time Resolved Reflectance and Transmittance for the Noninvasive Measurement of Tissue Optical Properties*, Patterson et al., Applied Optics, Vol. 28, No. 12, Jun. 15, 1989, Optical Society of America, incorporated in its entirety by reference herein. The Patterson article also provides an expression for the mean pathlength $$mpl = (4\mu_a D)^{-1/2} \frac{(d-z_0)e^{(2z_0\sqrt{\mu_a/D})} - (d+z_0)}{e^{(2z_0\sqrt{\mu_a/D})} - 1} \quad (13)$$

As equation (13) indicates, the mean pathlength is dependent on geometry and the concentration of various blood constituents and dynamically changes in tissue as the geometry and blood concentration changes. A way of dynamically determining the mean pathlength through a tissue sample is needed in order to reasonably estimate constituents such as blood glucose. Unfortunately, a measurement system such as described with respect to FIG. 3, above, is both large and expensive, confining its use to optical laboratories rather than clinical use. Instead, the pathlength measurement system of the present invention estimates the mean pathlength by measuring the magnetically-induced optical rotation of polarized light as it passes through a tissue sample.

One aspect of the present invention is a physiological monitor for measuring a blood constituent concentration within a tissue portion of a subject. The monitor has a polarized light source adapted to illuminate the tissue portion with an incident light beam and a magnetic field generator configured to impose a magnetic field on the tissue portion while illuminated by the light source. The magnetic field imparts a rotation in the plane of polarization of the incident light beam as it propagates through the tissue portion and emerges as a transmitted light beam. The monitor also has a polarimeter with an input responsive to the transmitted light beam and an output corresponding to the rotation. The monitor further has a signal processor in communications with the polarimeter output so as to compute an output corresponding to a mean pathlength estimate of the tissue portion. In one embodiment of the physiological monitor, the polarized light source and the polarimeter are adapted to provide spectroscopic measurements of the tissue portion, and the signal processor combines those spectroscopic measurements with corresponding mean pathlength estimates to provide an output indicative of the blood constituent concentration. In another embodiment of the physiological monitor, a separate spectrometer provides the spectroscopic measurements of the tissue portion and the signal processor provides corresponding mean pathlength estimates that are combined with the spectroscopic measurements to indicate the blood constituent concentration.

In yet another embodiment of the physiological monitor described in the above paragraph, the magnetic field generator alternately imposes a plurality of magnetic fields on the tissue portion. A first one of the fields encodes with a first rotation those photons traveling through the sample generally on-axis with the light beam. A second one of the fields encodes with a second rotation those photons traveling through the sample generally off-axis with the light beam. The mean pathlength measurement is a function of the second rotation relative to the first rotation. In a particular embodiment, the first one of the fields is a uniform field coaxial with the incident light beam and the second one of the fields is a uniform field orthogonal to the first one of the fields. In another particular embodiment, the first one of the fields is a uniform field coaxial with the incident light beam and the second one of said fields is a non-uniform field coaxial with the incident light beam. In yet another particular embodiment, the mean pathlength measurement is a ratio of the second rotation to the first rotation. In a further embodiment of the physiological monitor, the magnetic field generator alternately imposes a plurality of orthogonal magnetic fields on the tissue portion and the mean pathlength estimate is a function of a corresponding plurality of rotations in the plane of polarization of the incident light beam imparted by the fields. In a particular embodiment, the function is proportional to a square-root of a sum of the squares of the rotations.

Another aspect of the present invention is a physiological monitor for measuring a blood constituent concentration within a tissue portion of a subject having a light source adapted to illuminate the tissue portion with a monochromatic light polarized in a first direction and a magnetic field generator configured to alternately impose a first magnetic field and a second magnetic field on the tissue portion while illuminated by the light. The first field imparts a first rotation on the light and the second field imparts a second rotation on the light. The monitor also has a detector responsive to light intensity polarized in a second direction. The detector provides a first output corresponding to the first rotation and a second output corresponding to the second rotation so as to compensate for scattering in the tissue portion when calculating a blood constituent concentration. In one embodiment, the magnetic field generator is a Helmholtz coil configured to generate a first uniform magnetic field coaxially to the light source and a second uniform magnetic field orthogonally to the first uniform magnetic field. In another embodiment, the magnetic field generator is a pair of generally planar permanent magnets. The magnets are fixedly mounted parallel to each other and are rotatable between a first position that generates a first uniform magnetic field coaxially to the light source and a second position that generates a second uniform magnetic field orthogonally to the first uniform magnetic field. In yet another embodiment, the magnetic field generator is a pair of generally planar permanent magnets. The magnets are each hinged to move between a first position parallel to each other so as to generate a first uniform magnetic field coaxially to the light source and a second position tilted towards each other so as to generate a second non-uniform magnetic field coaxial to the light source.

A further aspect of the present invention is a physiological monitoring method for measuring a blood constituent concentration within a tissue portion of a subject. The method comprises the steps of illuminating the tissue portion with a polarized light beam, applying a magnetic field to the tissue portion, measuring a rotation in polarization of the light beam after transmission through said tissue portion, estimating a mean photon pathlength from the rotation and applying the mean pathlength to a spectroscopic measurement to determine the constituent concentration. In one embodiment, the method also comprises the steps of measuring an attenuation of light transmitted through the tissue portion and estimating an absorption from the result of the measuring. The applying step has the substeps of combining the mean photon pathlength and the absorption to compute a constituent concentration. In another embodiment, the method also has the steps of applying a second magnetic field to the tissue portion, measuring a second rotation in polarization of the light beam after transmission through the tissue portion, and calculating a ratio of the rotation and the second rotation so as to estimate a mean path length.

Yet another aspect of the present invention is a physiological monitor for measuring a blood constituent concentration within a tissue portion of a subject. The monitor comprises a light source means for illuminating the tissue portion with a polarized light beam and a generator means for imparting a rotation of the polarized light beam as it propagates through the tissue portion. The monitor also comprises a detector means for outputting a measure of the rotation and a processor means for utilizing, the measure to provide a compensation for scattering within the tissue portion. In one embodiment, the monitor further comprises a spectroscopic measurement means for providing an estimate of a blood constituent concentration within the tissue portion and a compensation means for combining the compensation with the estimate to improve the estimate.

BRIEF DESCRIPTION OF THE DRAWINGS

FIGS. 5A-D are graphical representations of a photon path within a uniform coaxial B-field, within uniform orthogonal B-fields and within a non-uniform coaxial B-field, respectively;

FIGS. 10A-B are perspective views of another embodiment of an optical spectroscopy pathlength measurement system utilizing a permanent magnet pair that has a parallel position (FIG. 10A) and an angled position (FIG. 10B);

DETAILS DESCRIPTION OF THE PREFERRED EMBODIMENT

Figure 4:
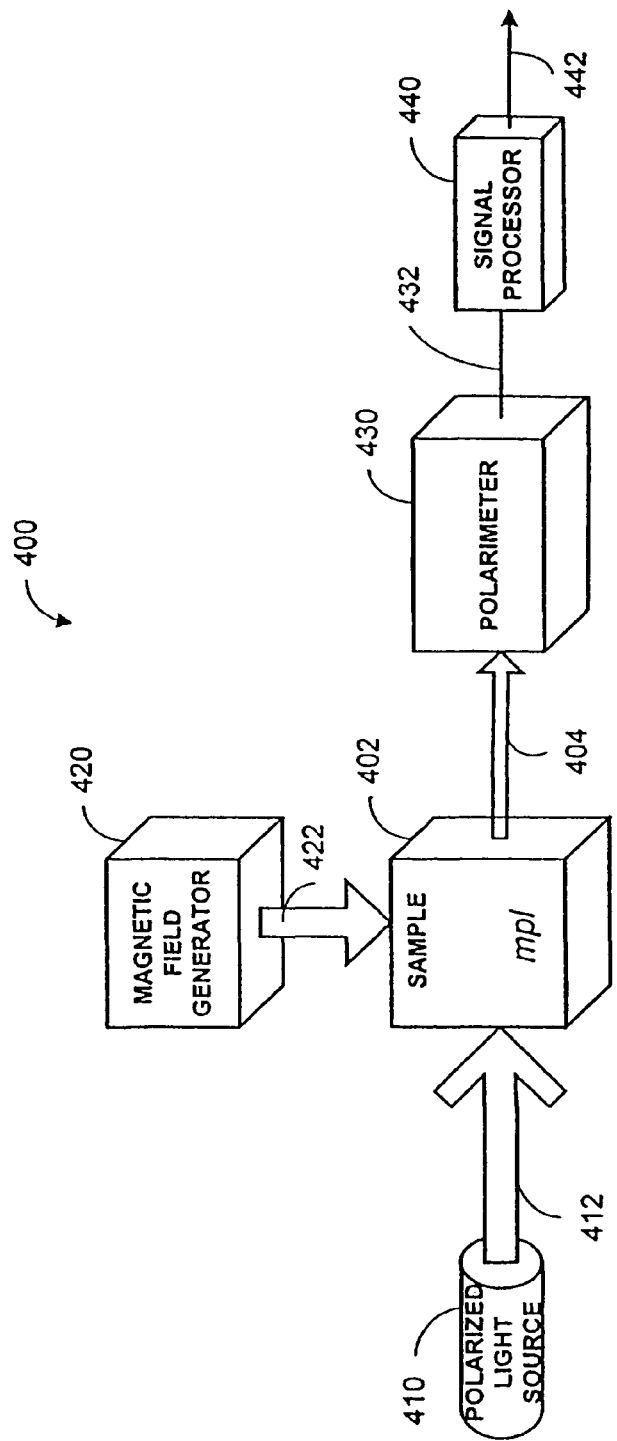
FIG. 4 is a block diagram of an optical spectroscopy pathlength measurement system according to the present invention.

FIG. 4 is a block diagram of an optical spectroscopy pathlength measurement system 400 according to the present invention. The pathlength measurement system 400 has a polarized light source 410, a magnetic field generator 420, a polarimeter 430 and a signal processor 440. The polarized light source 410 is adapted to illuminate a sample 402, which may be a tissue portion of a person, such as a fingertip. The polarimeter 430 is adapted to receive transmitted light 404 through the sample 402 and measure the polarization components of that light. The polarimeter output 432 is a measure of the optical rotation produced by the sample 402. The signal processor 440 inputs the polarimeter output 432 and provides an output 442 which is a computed estimate of the mean pathlength. Although this embodiment of a pathlength measurement system is based upon measuring light transmitted through the sample 402, as described by equation (7), one of ordinary skill in the art will recognize that a pathlength measurement system adapted to measure reflected light from the sample 402 could also be utilized for estimating mean pathlength and for measuring blood constituents.

As shown in FIG. 4, the magnetic field generator 420 is configured to generate a B-field 422 within the sample 402 during illumination by the polarized light source 410. The B-field 422 is imposed on the sample 402 to create a "Faraday effect," which causes rotation in the plane of polarization of a linearly-polarized beam of light as it propagates through a medium in the presence of a magnetic field. Due to the Faraday effect, the B-field 422 rotates the plane of polarization of the light source 410. The amount of optical rotation is given by $$\phi = \int \upsilon \vec{B} \cdot d\vec{l} \tag{14}$$

where $\upsilon$ is the Verdet constant, which depends on the material and the wavelength. The direction of rotation depends on whether light is traveling parallel or anti-parallel to the B-field. Hence, the rotation is cumulative, i.e. does not reverse when the direction of propagation reverses. One or more B-fields 422 can be used to differentially encode with rotation those photons traveling generally on-axis and generally off-axis through the sample 402. Optical rotation is measured by the polarimeter 430 and used by the signal processor 440 to estimate the mean optical pathlength, mpl, of the sample 402, as described in further detail below.

Figure 1:
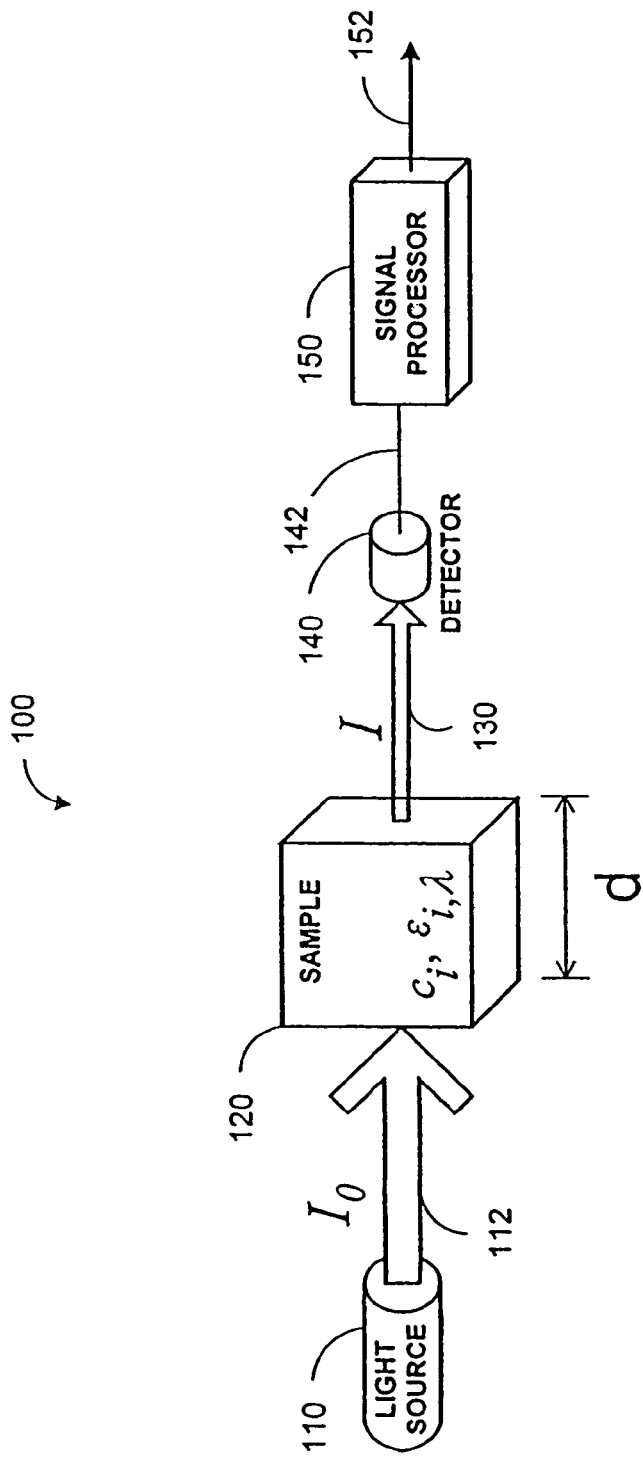
FIG. 1 is an illustration depicting a conventional optical spectroscopic measurement system for determining the concentration of various constituents within a sample.

Shown in FIG. 4, the polarized light source 410 and polarimeter 430 can be configured as a variable wavelength light source 110 (FIG. 1) and a detector 140 (FIG. 1) for making simultaneous spectroscopic measurements. Alternatively, the pathlength measurement system 400 can be integrated with a separate spectroscopic measurement system 100 (FIG. 1). In either case, the pathlength estimates provided by the pathlength measurement system 400 can be combined with spectroscopic measurements to compensate for scattering in the sample 402 when estimating absorbing constituent concentrations in the sample 402.

Also shown in FIG. 4, without scattering, the transmitted light 404 emerging from the sample 402 has the same polarization as the incident light 412 emitted from the polarized light source 410. The cumulative effect of scattering in the sample 402, however, is to depolarize a significant portion of the incident light 412. The amount of depolarization is a function of the amount of scattering that occurs. To account for this depolarization, the polarimeter output 432 can be normalized by the ratio of the intensities of the polarized light to the unpolarized light or the ratio of the polarized light intensity to the total intensity.

Figure 2:
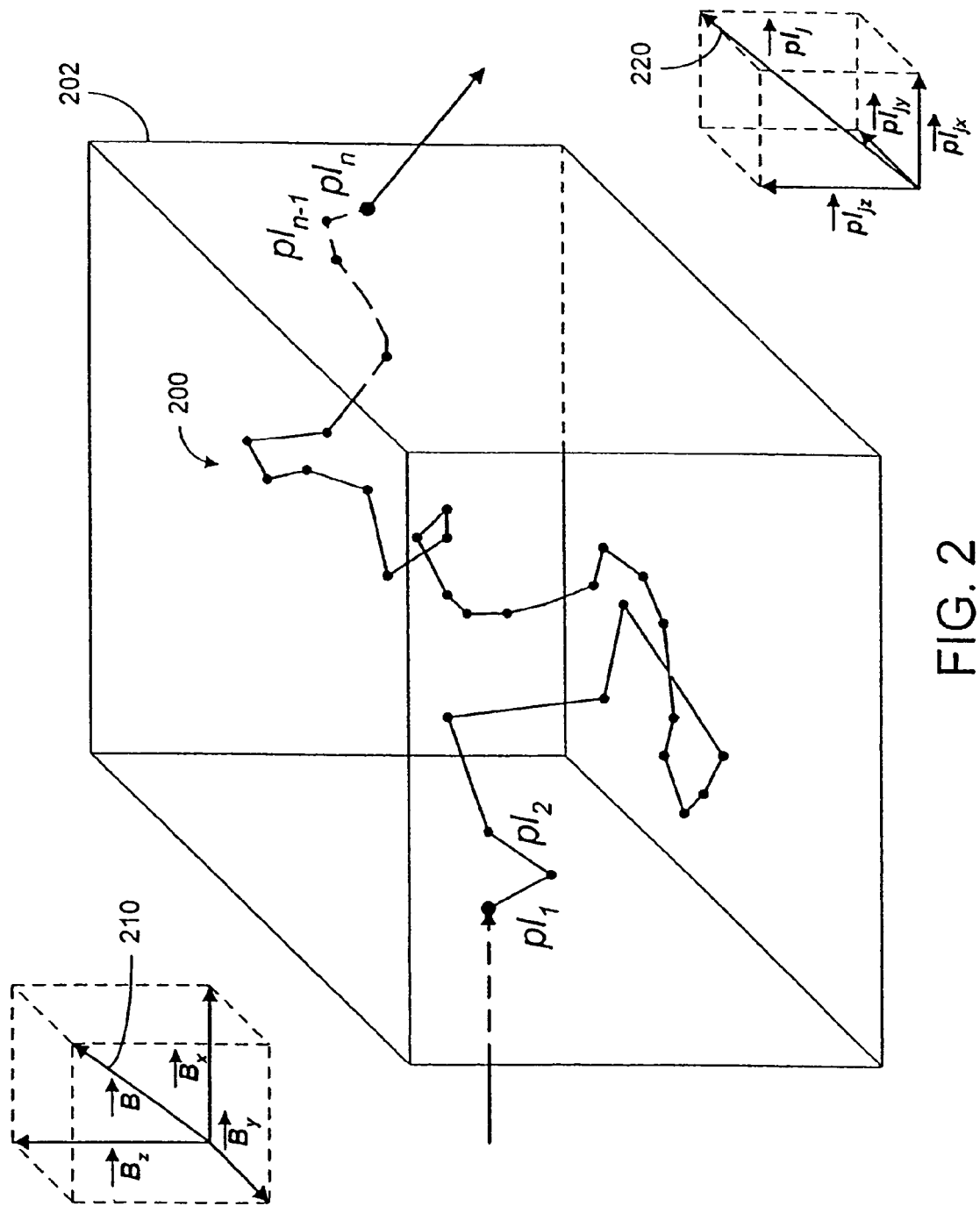
FIG. 2 is an illustration depicting a photon path through a turbid medium and a component of the photon path projected onto orthogonal components of a uniform B-field.
Figure 3:
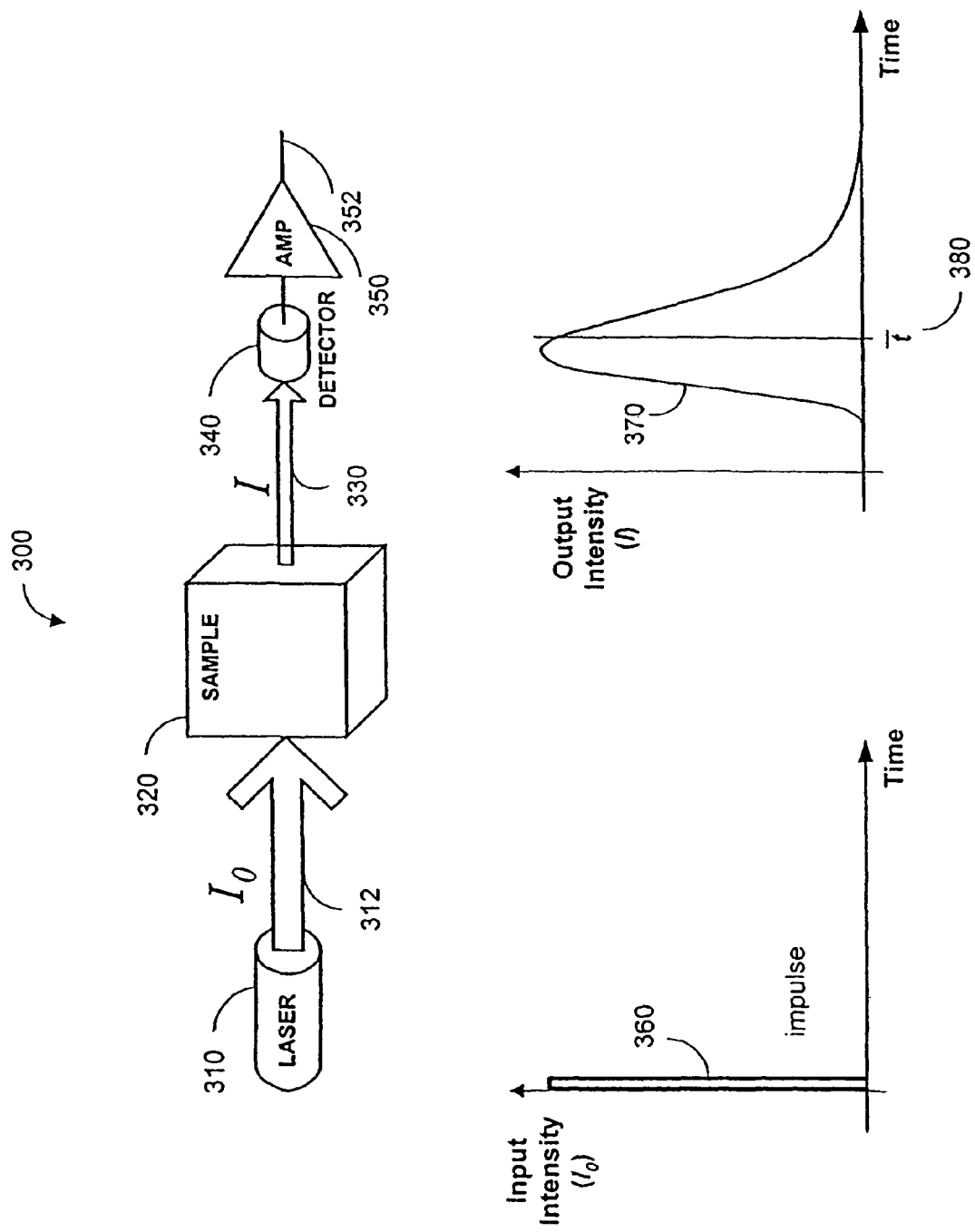
FIG. 3 is a diagram illustrating the mean optical pathlength through a sample.

As FIG. 2 illustrates, when a uniform magnetic field $\vec{B}$ 210 is applied to a medium 202 an optical rotation $\phi_i$ is imparted to the photon while traversing a particular path segment $\vec{p}\,l_j$ 220. The optical rotation is computed from the projection of $\vec{p}\,l_j$ onto $\vec{B}$ according to equation (14), which can be written in terms of the orthogonal components of $\vec{p}\,l_j$ and $\vec{B}$ as $$\phi_j = \upsilon \sqrt{(B_x p l_{jx})^2 + (B_y p l_{jy})^2 + (B_z p l_{jz})^2} \tag{15}$$

The total optical rotation through the sample is $$\phi = \sum_{i=1}^{n} \phi_i \tag{16}$$

Figure 5A:
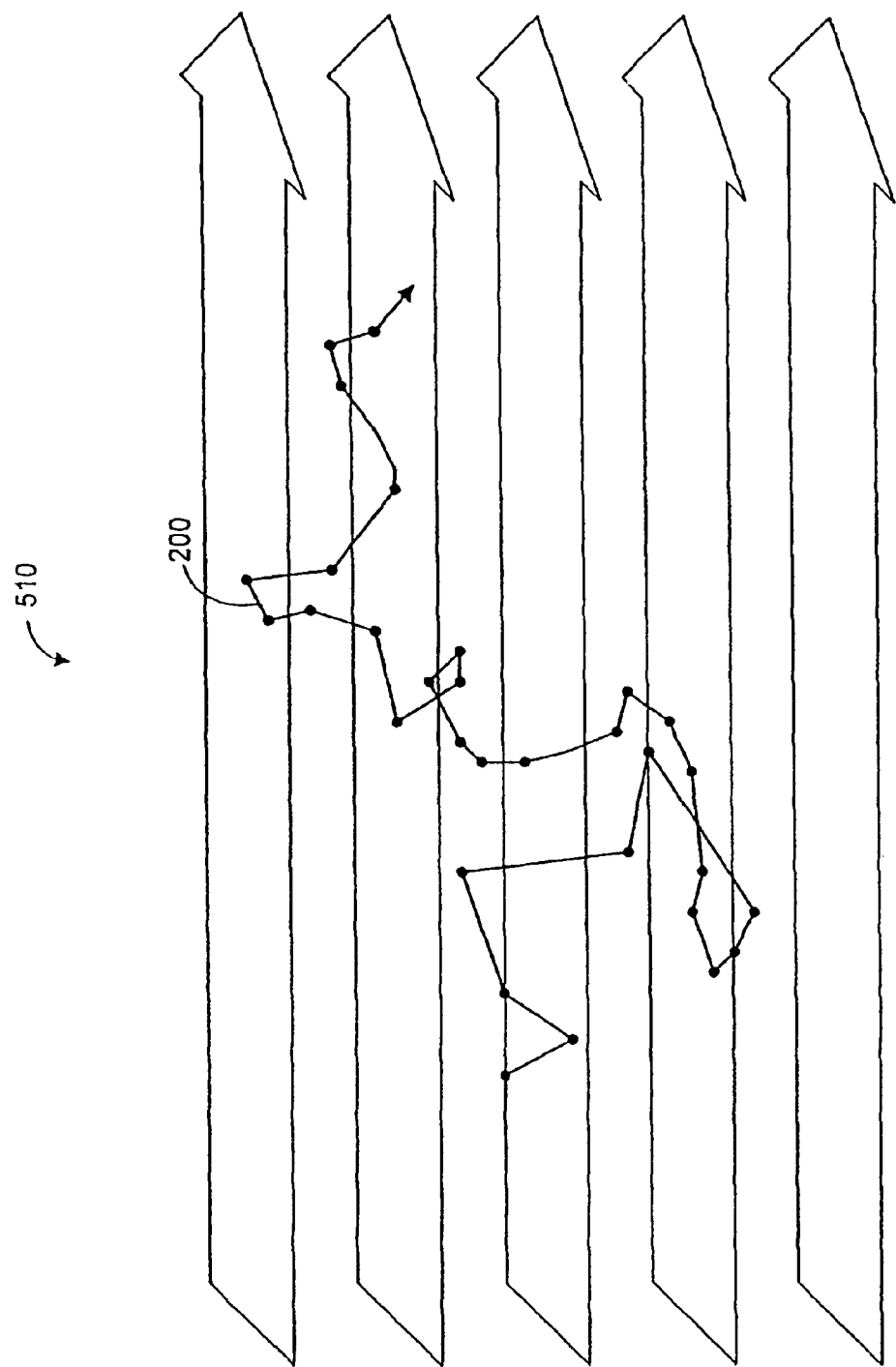
Figure 5B:
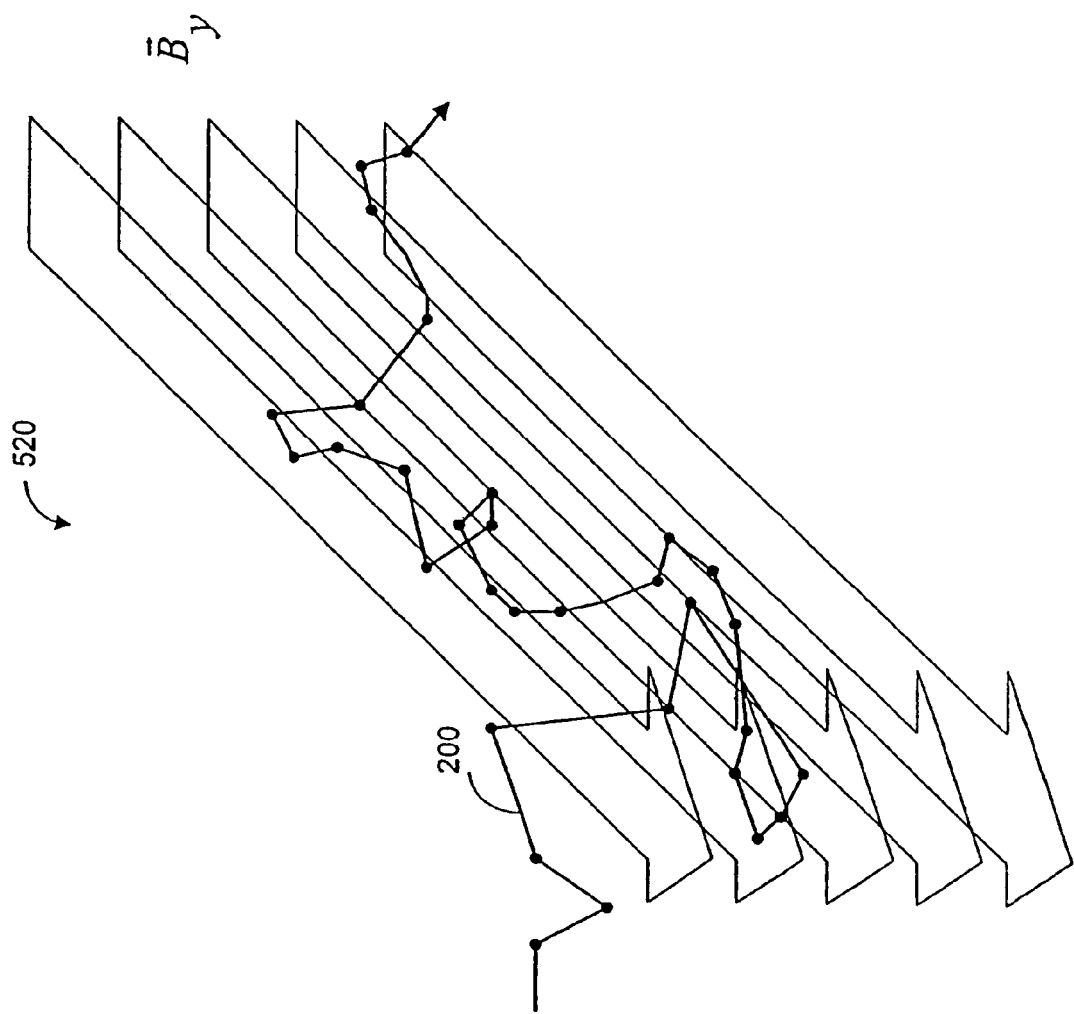

FIGS. 5A-5C illustrate the alternate application of uniform orthogonal B-fields, $\vec{B}_x$ 510 (FIG. 5A), $\vec{B}_y$ 520 (FIG. 5B), and $\vec{B}_z$ 530 (FIG. 5C) to a photon path 200 through a sample 202 (FIG. 2). This results in three optical rotation measurements, which according to equation (15) and equation (16) are $$\phi_x = \upsilon B_x \sum_{i=1}^{n} |pl_{ix}|; \quad \phi_y = \upsilon B_y \sum_{i=1}^{n} |pl_{iy}|; \quad \phi_z = \upsilon B_z \sum_{i=1}^{n} |pl_{iz}| \tag{17}$$

The pathlength as expressed in equation (6) can be estimated as follows $$pl \approx \sqrt{\left(\sum_{i=1}^{n} |pl_{ix}|\right)^2 + \left(\sum_{i=1}^{n} |pl_{iy}|\right)^2 + \left(\sum_{i=1}^{n} |pl_{iz}|\right)^2} \tag{18}$$

which underestimates the sum of the magnitudes of the individual pathlength vectors by the magnitude of the sum of the vector projections along each orthogonal axis. Combining equations (17) and (18) yields $$mpl \approx \frac{1}{\upsilon B} \sqrt{\phi_x^2 + \phi_y^2 + \phi_z^2} \tag{19}$$

which provides an estimate of the mean path, mpl, in terms of the measured optical rotations due to alternately applied orthogonal, uniform B-fields of equal magnitude B. Assuming that the incident beam is along the x-axis and that scattering in the sample is uniform off axis, equation (19) can be simplified with an estimate of mean pathlength based on the alternate application of a uniform on-axis B-field and an orthogonal off-axis B-field $$mpl \approx \frac{1}{\upsilon B} \sqrt{\phi_x^2 + 2\phi_y^2} \tag{20}$$

Assuming that the incident beam is along the x-axis and the dominate term is the projection of the photon paths onto the x-axis, equation (20) can be further simplified with an estimate of mean path length based on the application of a uniform on-axis B-field $$mpl \approx \frac{\phi_x}{\upsilon B} \tag{21}$$

A problem with the mean pathlength estimates expressed in equations (19) through (21) is the dependence on the Verdet constant, which varies with the sample constituents and wavelength. Accordingly, an alternative mean pathlength estimate can be expressed as a ratio that is used as a multiplier of the geometric pathlength d to account for the increased optical pathlength due to scattering $$mpl \approx d\alpha\rho \tag{22}$$

where α is a constant that cancels when a ratio of constituent concentrations is computed, as described with respect to FIG. 12, below. In one embodiment, the ratio ρ is $$\rho = \frac{\sqrt{\phi_x^2 + \phi_y^2 + \phi_z^2}}{\phi_x} \tag{23}$$

so that the estimate of the mean path length is increased as the off-axis rotation components become more significant. An alternative estimate, which is simpler to measure is $$\rho = \frac{\phi_y}{\phi_x} \tag{24}$$

Figure 6A:
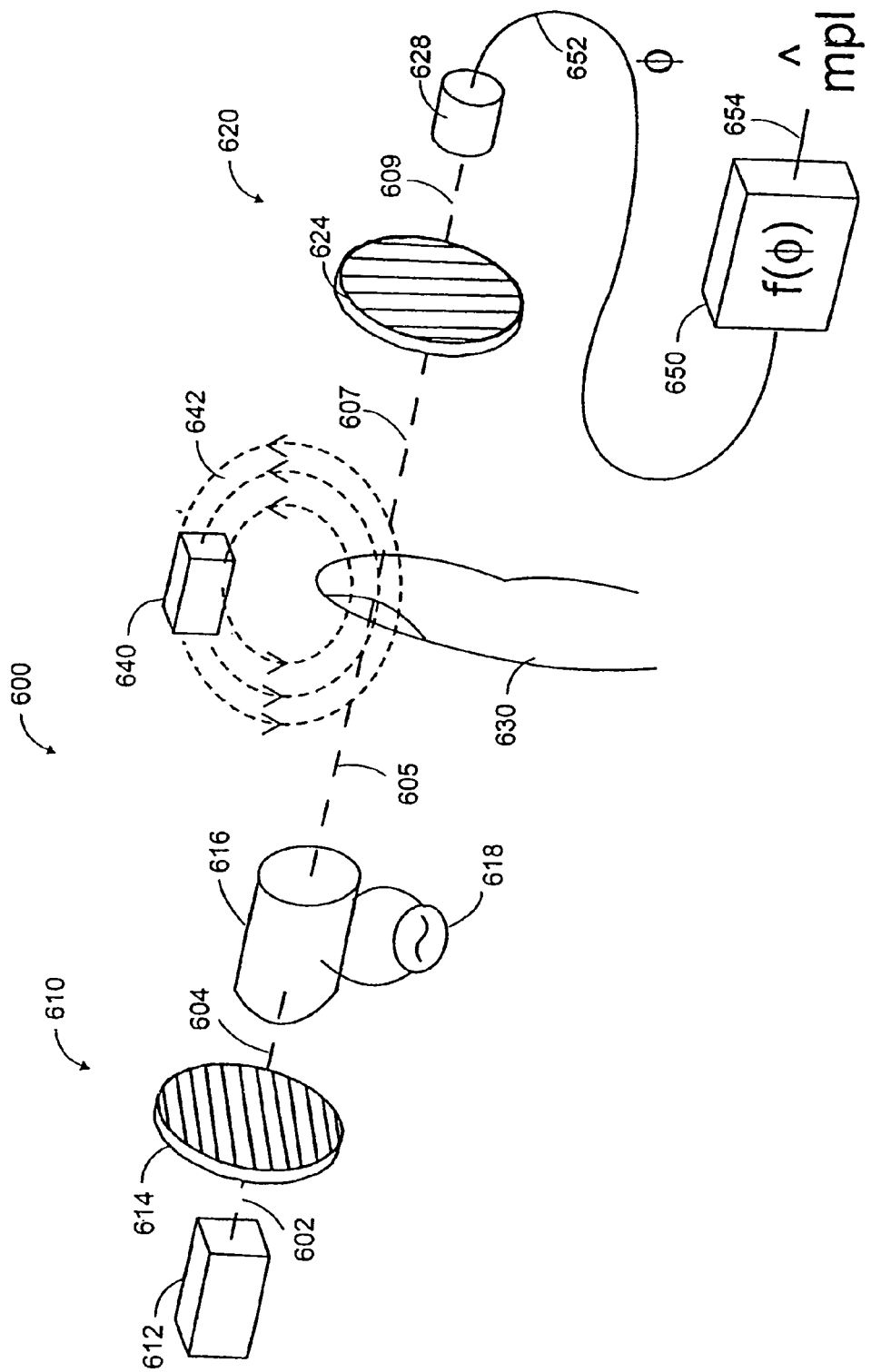
FIGS. 6A-B are illustrations depicting particular embodiments of an optical spectroscopy pathlength measurement system incorporating a faraday rotation modulator and a photoelastic modulator, respectively.

FIG. 6A is an illustration depicting a Faraday rotator modulator embodiment of an optical spectroscopy pathlength measurement system 600 according to the present invention. The pathlength measurement system 600 has a polarized light source 610 and an optical rotation sensor 620. The polarized light source 610 and the optical rotation sensor 620 together form a polarimeter. The polarized light source 610 illuminates a sample 630, which may be a tissue portion of a person, such as the fingertip shown. The optical rotation sensor 620 receives light transmitted through the sample 630. A magnet field generator 640 creates a B-field 642 within the sample 630 during illumination by the light source 610.

Also shown in FIG. 6A, the polarized light source 610 has a multiple wavelength optical emitter 612, a first polarizer 614, and a modulator 616. The optical rotation sensor 620 has a second polarizer 624 and a detector 628. The emitter 612 radiates a beam 602 through a first polarizer 614, which has its polarization axis oriented at a reference angle, shown as 0° from the horizontal plane. The electric field from the beam 602 is linearly polarized by the first polarizer 614. In order to reduce system noise, the polarized beam 604 passes through a Faraday rotator modulator 616. The modulator is driven by a sinusoidal source 618 that phase modulates the electric field of the polarized beam 604. The modulated beam 605 passes through the sample 630 where it obtains a optical rotation φ. The rotated beam 607 then passes through the second polarizer 624, which has its polarization axis aligned orthogonally from that of first polarizer 614. Due to the optical rotation, the rotated beam 607 has an electrical field component along the axis of the second polarizer 624. The output beam 609 from the second polarizer 624 is then measured by a detector 628, such as a photodiode. The electric field of the output beam 609 can be expressed as $$E(t) = E_0 \sin[\phi + \theta_m \sin(\omega_m t)] \tag{25}$$

where $\omega_m$ is the modulation frequency and $\theta_m$ is the modulation amplitude. Therefore, the irradiance measured by the detector 628, which is proportional to the square of the electrical field E(t) of the output beam 609 is $$I(t) = E_0^2 \left(\frac{c\varepsilon_0}{2}\right) \sin^2[\phi + \theta_m \sin(\omega_m t)] \tag{26}$$

Equation (26) can be simplified using the following identity $$\sin^2 x = \frac{1 - \cos(2x)}{2} \tag{27}$$

From equation (26) and equation (27)

$$I(t) = E_0^2 \left(\frac{c\varepsilon_0}{2}\right) \left\{\frac{1 - \cos[2\phi + 2\theta_m \sin(\omega_m t)]}{2}\right\} \tag{28}$$

Assuming the angle of the cosine in equation (28) is small, the cosine may be approximated with the first two terms of its Taylor series expansion $$\cos(x) \cong 1 - \frac{x^2}{2} \tag{29}$$

As a result, the detector output 652 is $$I(t) = \kappa_d E_0^2 \left(\frac{c\varepsilon_0}{2}\right) \left\{\phi^2 + 2\phi\theta_m \sin(\omega_m t) + \frac{\theta_m^2[1 - \cos(2\omega_m t)]}{2}\right\} \tag{30}$$

where $\kappa_d$ is the detector gain. The desired quantity, φ, occurs at the modulation frequency, which can be obtained by high pass filtering the DC term and using a lock-in amplifier (not shown) from the detector output 652 to control the sinusoidal source 618, as is well-known in the art. Thus, the detector output 652 provides a signal proportional to the optical rotation within the sample 630.

Figure 6B:
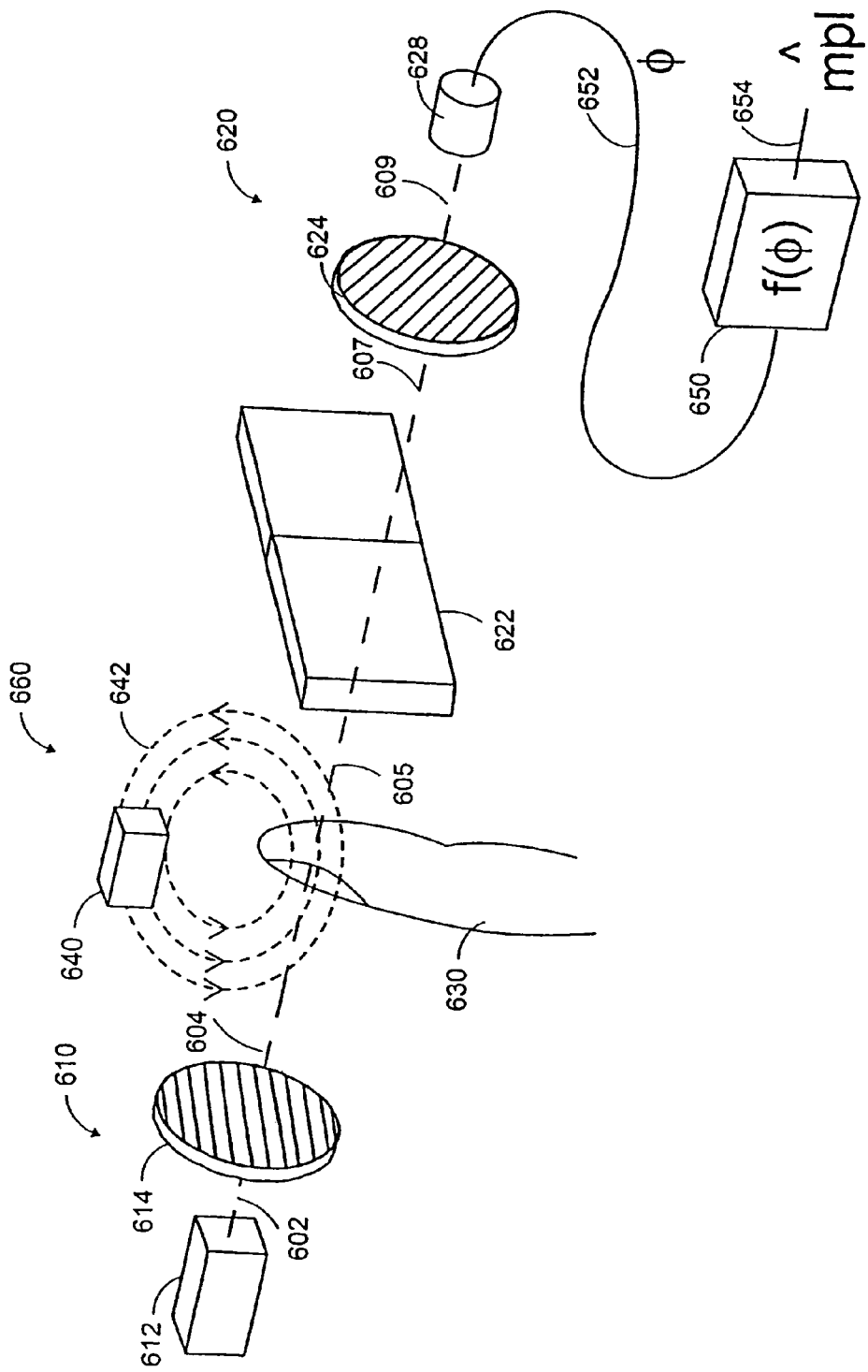

FIG. 6B is an illustration depicting a photoelastic modulator (PEM) embodiment of an optical spectroscopy pathlength measurement system 660 according to the present invention. The pathlength measurement system 660 has a polarized light source 610, and an optical rotation sensor 620, and a magnet field generator 640 that function generally as described above with respect to FIG. 6A. In the embodiment of FIG. 6B, the polarized light source 610 has a multiple wavelength optical emitter 612 and a first polarizer 614 oriented at 0°. The optical rotation sensor 620 has a PEM 622, a second polarizer 624 oriented at 45° and a detector 628. The emitter 612, first polarizer 614 and detector 628 also function generally as described above with respect to FIG. 6A. The first polarizer 614 is oriented parallel to the PEM 622 axis. If no rotation occurs, no component of the polarization at 45° to the PEM 622 axis will occur. Hence, no modulated signal will be measured by the detector 628. Any rotation would result in a detected signal, which for small angles is proportional to the angle of rotation.

Figure 7:
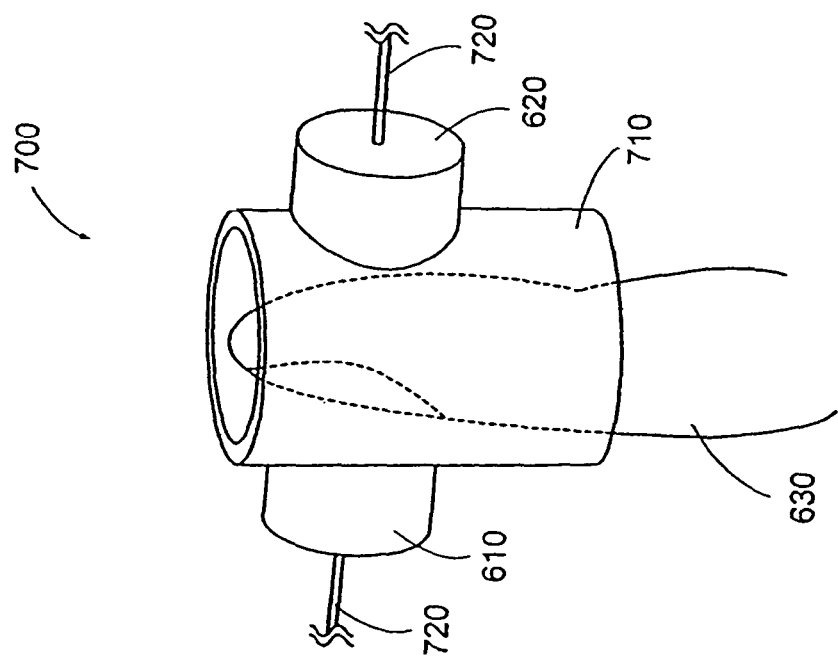
FIG. 7 is a perspective view of a polarimeter portion of an optical spectroscopy pathlength measurement system.

FIG. 7 illustrates the polarimeter portion of the optical spectroscopy pathlength measurement system. The polarimeter 700 has a body 710, a light source 610 and a rotation sensor 620. In one embodiment, the body 710 is a hollow cylinder adapted to accept a fingertip 630. The body 710 integrates the light source 610 and the rotation sensor 620, which have ends terminating at opposite sides of the body 710. The light source 610 and the rotation sensor 620 are configured so that a beam from the light source 610 will illuminate a fingertip placed within the body 710 and so that a corresponding beam emerging from the fingertip will be received by the rotation sensor 620. Wiring 720 extending from the light source 610 and rotation sensor 620 provide power and signal paths, respectively.

Figure 8:
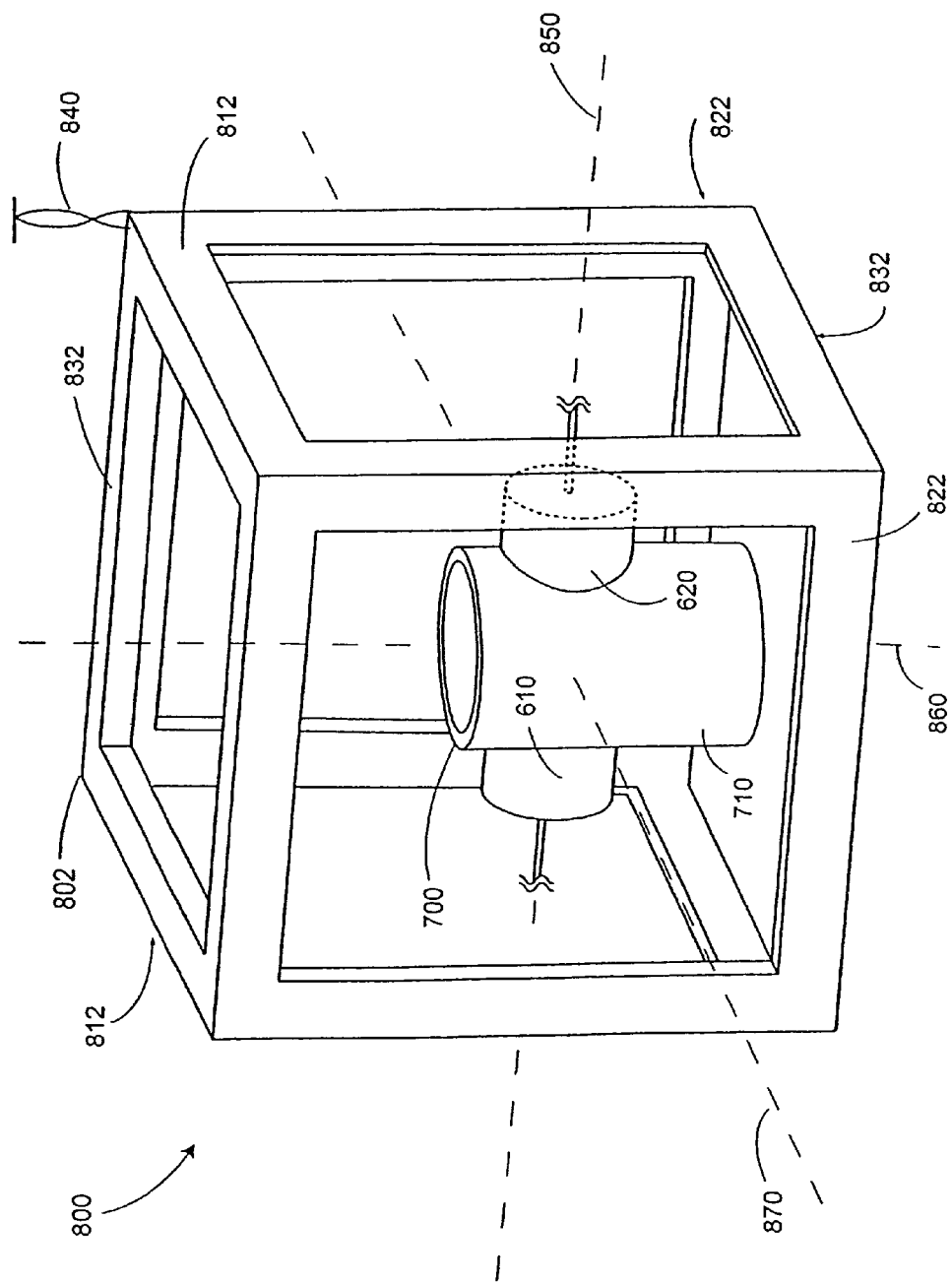
FIG. 8 is a perspective view of one embodiment of an optical spectroscopy pathlength measurement system utilizing a triaxial Helmholtz coil for magnetic field generation.

FIG. 8 illustrates an embodiment of the optical spectroscopy pathlength measurement system 800 utilizing a triaxial Helmholtz coil for magnetic field generation. The pathlength measurement system 800 has a polarimeter portion 700 enclosed by a triaxial Helmholtz coil 802. A Helmholtz coil is a pair of coaxially mounted electromagnetic coils separated by a distance equal to the coils' diameter. When excited by coil currents in the same direction, the magnetic fields add in a manner that produces a very uniform magnetic field along the common axis of the coils, as is well-known in the art.

Shown in FIG. 8 are three Helmholtz coil pairs, including an x-axis pair 812, a y-axis pair 822, and a z-axis pair 832 mounted along mutually orthogonal axis to form a cube. Electrical current to energize the coils is routed independently to each of the three coil pairs 812, 822, 832 via a cable 840. The polarimeter 700 is oriented within the Helmholtz coil 802 so that the light beam from the light source 610 to the rotation sensor 620 is aligned with the x-axis 850 and the body 710 is coaxial with the z-axis 860. With this configuration, each of the three coil pairs 812, 822, 832 can generate uniform, orthogonal B-fields within a fingertip inserted into the body 710. Hence, the three coil pairs 812, 822, 832 are alternately energized during operation of the polarimeter 700 to measure the resulting optical rotations and to estimate the mean pathlength through a fingertip sample according to equation (19). With this same configuration, the x-axis coil pair 812 and the y-axis coil pair 822 are alternately energized during operation of the polarimeter 700 to measure the resulting optical rotations and to estimate the mean pathlength through a fingertip sample according to equation (20). Similarly, the x-axis coil pair 812 is energized during operation of the polarimeter 700 to measure the resulting optical rotation and to estimate the mean pathlength through a fingertip sample according to equation (21).

Figure 9:
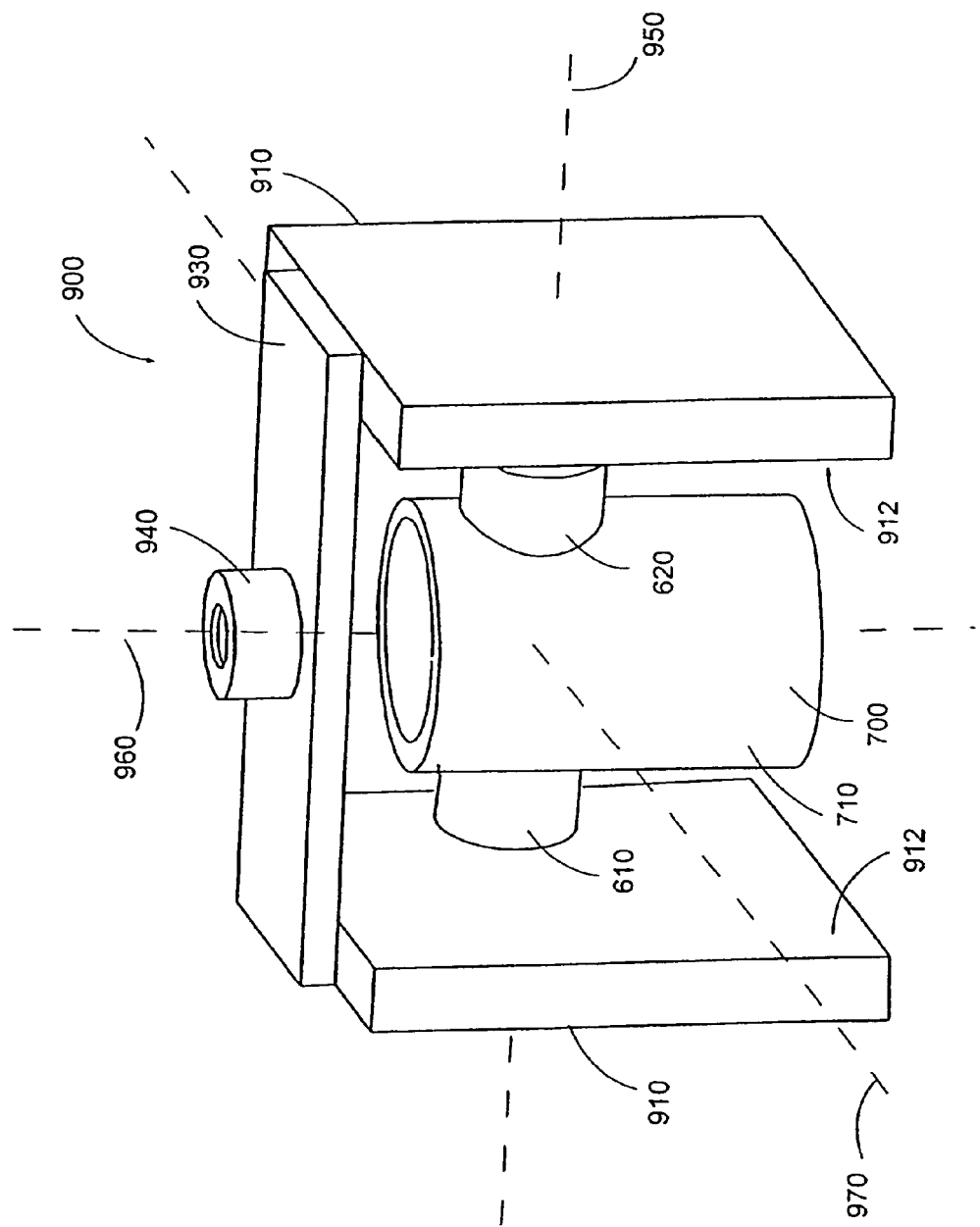
FIG. 9 is a perspective view of another embodiment of an optical spectroscopy pathlength measurement system utilizing a permanent magnet pair for magnetic field generation.

FIG. 9 illustrates another embodiment of an optical spectroscopy pathlength measurement system 900 utilizing a permanent magnet pair for magnetic field generation. The pathlength measurement system 900 has a polarimeter portion 700 mounted within a pair of permanent magnets 910, each having a planar face 912. The permanent magnet pair 910 is connected by a crossbar 930 of nonmagnetic material, and a knob 940 is mounted atop the crossbar 930. The polarimeter 700 is oriented between the magnets 910 so that the light beam from the light source 610 to the rotation sensor 620 is aligned with the x-axis 950 and the cavity of the body 710 is coaxial with the knob 940 and the z-axis 960. The magnets 910 are rotatable about the z-axis 960 from a first position where the faces 912 are normal with the x-axis 950 to a second position where the faces 912 are normal with the y-axis 970.

With this configuration, the rotatable magnets 910 can generate uniform, orthogonal B-fields oriented along the x-axis 950 and y-axis 970 within a fingertip inserted into the body 710. Hence, the rotatable magnets 910 are alternately rotated between the first position (shown) and the second position during operation of the polarimeter 700 to measure the resulting optical rotations and to estimate the mean pathlength through a fingertip sample according to equation (20). With this same configuration, the magnet pair 910 can remain in the first position (shown) during operation of the polarimeter 700 to measure the resulting optical rotation and to estimate the mean pathlength through a fingertip sample according to equation (21).

FIGS. 5A and 5D depict a photon path 200 within uniform 510 (FIG. 5A) and non-uniform 540 (FIG. 5D) coaxial B-fields. As shown in FIG. 5A, a photon propagates along path 200 as the result of an incident beam aligned with the x-axis. Scattering within the illuminated medium results in the path 200 deviating off-axis in a random manner. A uniform field $\vec{B}_x$ 510 (FIG. 5A) imparts a first rotation to the incident beam, which is measured with a polarimeter as described with respect to FIG. 6A and FIG. 6B, above. As shown in FIG. 5D, a non-uniform field $\vec{B}_x'$ 540 imparts a second rotation to the incident beam, which is also measured with the polarimeter. The non-uniform field 540 (FIG. 5D) is devised so that the field strength is greater off-axis. The non-uniform field 540 (FIG. 5D) acts to encode photons that deviate more off-axis with a proportionately larger optical rotation as compared to photons that remain relatively on-axis, i.e. "snake photons." The uniform field 510 (FIG. 5A) acts as a reference, i.e. provides a reference rotation for unencoded photons. Thus, the following ratio can be used in conjunction with equation (22) to form an estimate of the mean path length.

$$\rho = \frac{\phi_n}{\phi_u} \quad (31)$$

where $\phi_n$ and $\phi_u$ are the measured optical rotations in the presence of the non-uniform and the uniform B-fields, respectively.

Figure 10A:
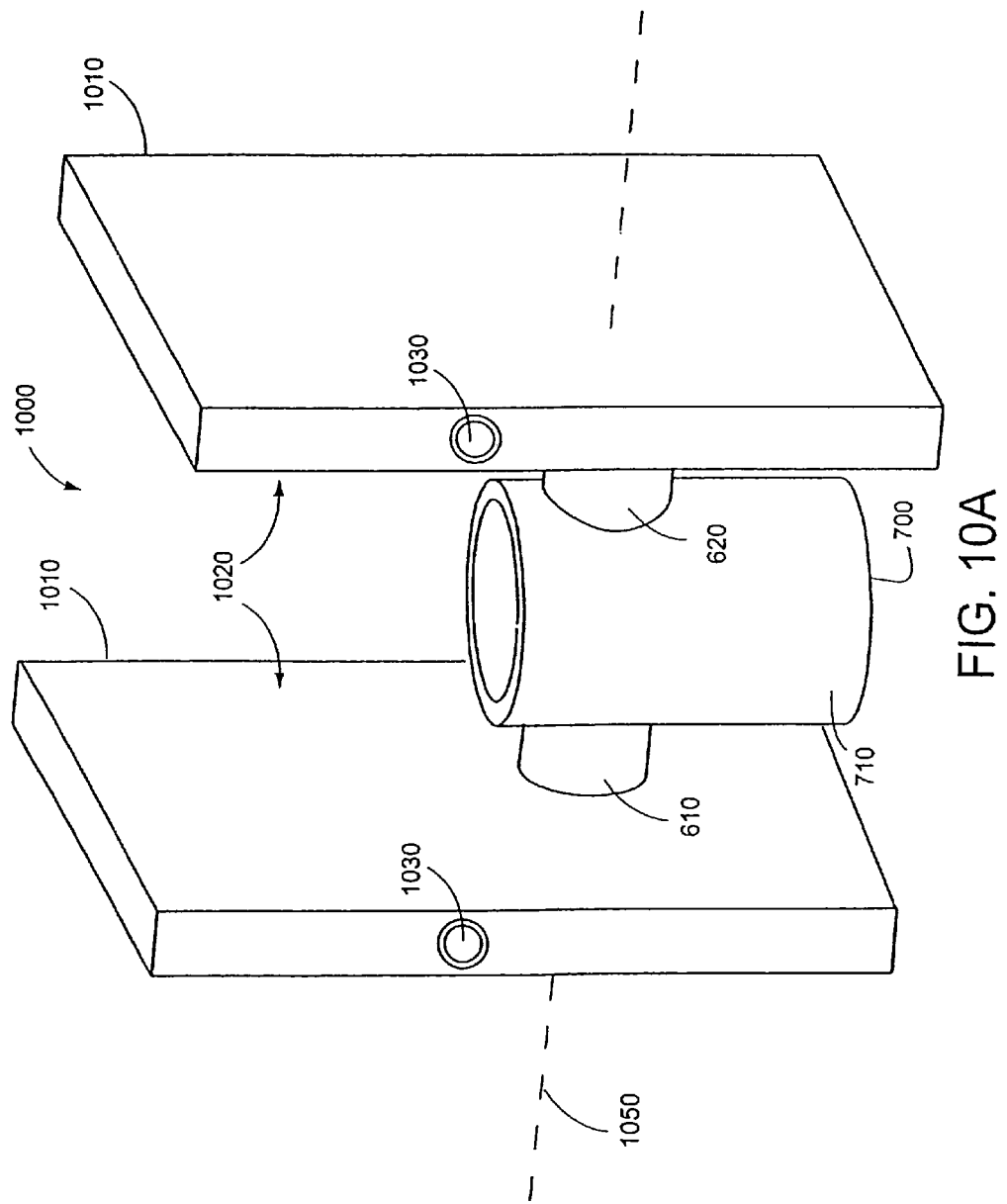

FIGS. 10A-B illustrate another embodiment of an optical spectroscopy pathlength measurement system 1000 utilizing a permanent magnet pair that creates both a uniform and a non-uniform magnet field. The pathlength measurement system 1000 has a polarimeter portion 700 mounted within a pair of permanent magnets 1010. Each magnet 1010 has a generally planar face 1020 and a hinge 1030. The hinges 1030 allow the magnets to be moved between a parallel position, as shown in FIG. 10A, and an angled position, as shown in FIG. 10B. The polarimeter 700 is oriented between the magnets 1010 so that the light beam from the light source 610 to the rotation sensor 620 is aligned with the x-axis 1050, which is normal to the magnet faces 1020 in the parallel position.

With this configuration, the hinged magnets 1010 in the parallel position (FIG. 10A) generate a uniform B-field within a fingertip inserted into the body 710. The hinged magnets 1010 in the angled position (FIG. 10B) generate a non-uniform B-field within the fingertip. Hence, the hinged magnets 1010 are alternately tilted between the parallel position (FIG. 10A) and the angled position (FIG. 10B) during operation of the polarimeter 700 to measure the resulting optical rotations and to estimate the mean pathlength through a fingertip sample according to equation (31).

Figure 11:
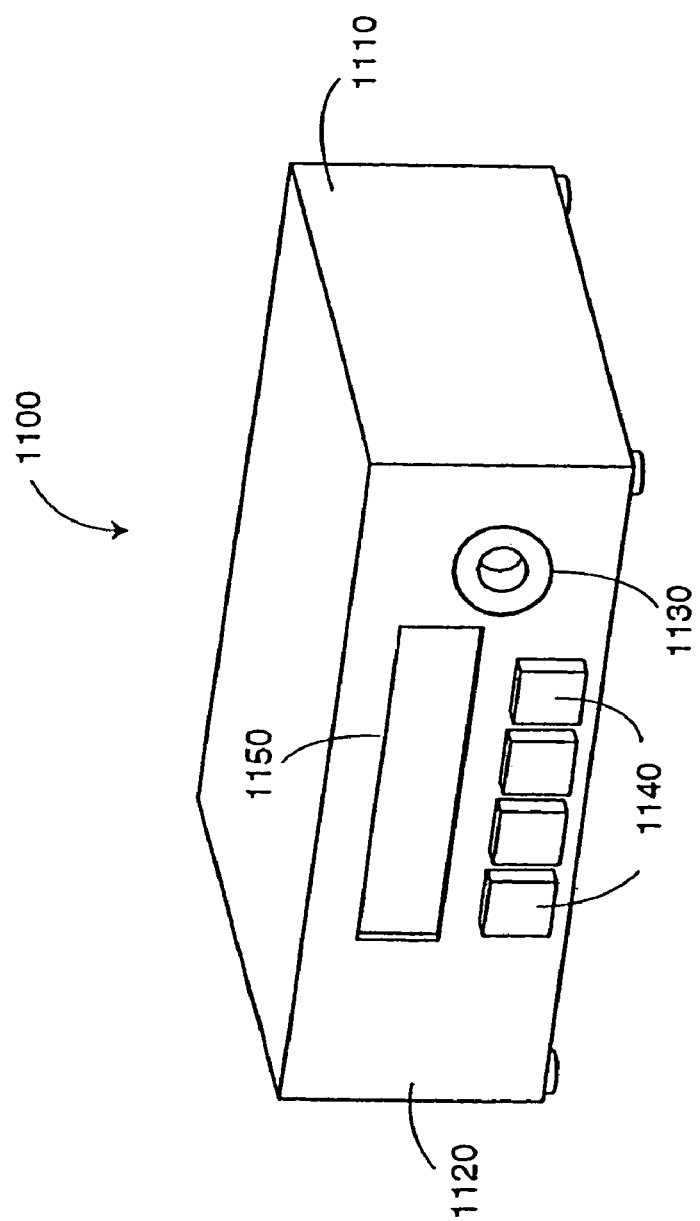
FIG. 11 is a perspective view of a blood constituent measurement instrument incorporating an optical spectroscopy pathlength measurement system according to the present invention.

FIG. 11 illustrates a noninvasive blood constituent measurement instrument 1100 incorporating an optical spectroscopy pathlength measurement system according to the present invention. The instrument 1100 has a chassis 1110 including a front panel 1120. The front panel 1120 has a sample area 1130, control keys 1140 and a display 1150. The chassis 1110 houses a pathlength measurement system including a signal processor and an associated power supply.

The polarimeter portion 700 (FIG. 7) is mounted to the front panel 1120 behind the sample area 1130 so that a fingertip can be inserted into the sample area 1130 for noninvasive blood constituent measurements. The associated B-field generator 420 (FIG. 4), such as the triaxial Helmholtz coils 802 (FIG. 8), rotatable magnets 910 (FIG. 9) or hinged magnets 1010 (FIGS. 10A-B) are also mounted to the front panel 1120 proximate the polarimeter 700 (FIG. 7). In operation, a person places their fingertip into the sample area 1130 and initiates a measurement by pressing a key 1140. The polarimeter and magnets are activated to perform spectroscopy and mean path length measurements, as described with respect to FIG. 12, below. The internal signal processor processes these measurements to compute a blood constituent concentration value, as described with respect to FIG. 12, below. The blood constituent value is then provided to the person as a reading on the display 1150.

Figure 12:
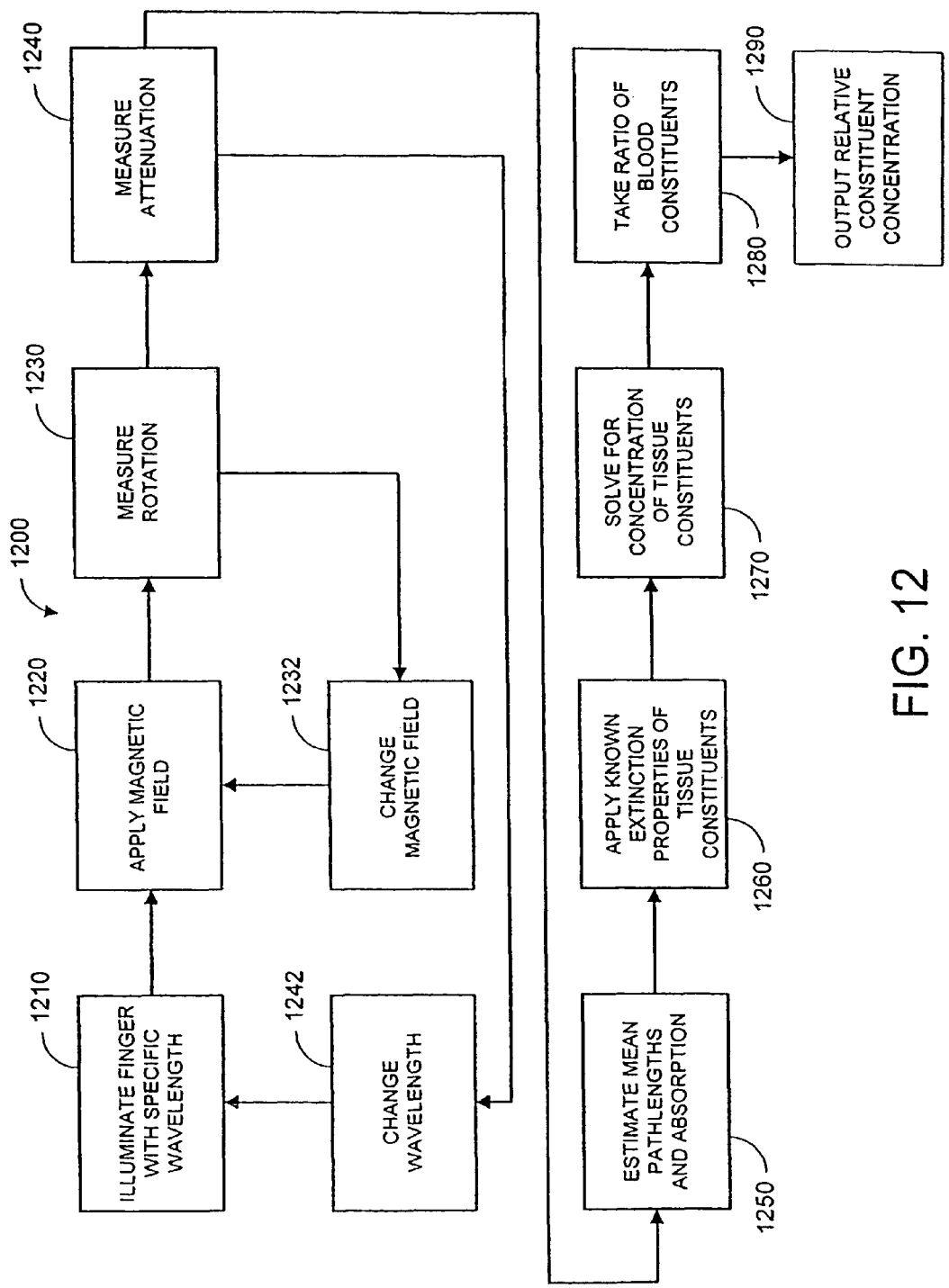
FIG. 12 is a functional block, diagram of a blood constituent measurement instrument.

FIG. 12 provides a functional block diagram of a noninvasive blood constituent measurement instrument 1100 (FIG. 11). When a blood constituent measurement is initiated, the polarimeter light source 610 (FIGS. 6A-B) illuminates the fingertip with a predetermined wavelength 1210. Multiple wavelength optical emitter embodiments, including a broadband optical source transmitting through a filtering element are described in U.S. Pat. No. 5,743,262 entitled "Blood Glucose Monitoring System," which is assigned to the assignee of the present invention and incorporated herein by reference. At the same time the fingertip is illuminated, a magnetic field is applied 1220 to induce the Faraday effect. The resulting optical rotation is measured 1230 by the rotation sensor 620 (FIGS. 6A-B). Further, light intensity attenuation is also measured 1240 by the rotation sensor detector 628 (FIGS. 6A-B). Depending on the method used to estimate mean pathlength, the magnetic field may be changed 1232 and further rotation measurements made 1230. Depending on the number of constituents to be resolved, the wavelength of the light source is changed 1242 and the process described above is repeated for each wavelength used. Each of the optical rotation 1230 and attenuation measurements 1240 are filtered, amplified and digitized at the output of the rotation sensor detector 628 (FIGS. 6A-B).

As shown in FIG. 12, the resulting digital values from the detector are processed by a signal processor 650 (FIGS. 6A-B). The processor applies one or more of equations (19)-(24), (31) to estimate the mean pathlength 1250 at each applied wavelength. The processor also computes the tissue sample absorption at each wavelength 1250. The processor recalls from memory predetermined extinction properties for the tissue constituents 1260 for each applied wavelength. The processor then solves equation (10) or equivalent to determine the constituent concentrations 1270. As noted above, these concentrations may only be determinable to within an unknown constant, which cancels when a concentration ratio 1280 is computed. For example, the ratio of the computed concentration for glucose to the computed concentration for water can be calculated to provide an absolute glucose concentration. Finally, the relative constituent concentration is provided as an output 1290 to the instrument display or to another connected medical instrument or display.

The optical spectroscopy pathlength measurement system has been disclosed in detail in connection with various embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. An optical pathlength measurement system for determining a pathlength of a light source passing through a tissue sample comprising:
   an optical emitter for emitting light of one or more wavelengths;
   a first filter for filtering the light emitted from the optical emitter;
   a magnetic field generator for optically rotating the light as it passes through a tissue sample;
   a second filter for filtering the light after it passes through the tissue sample;
   a detector for detecting the light after it passes through the second filter; and
   a processor for determining and outputting a pathlength of the light emitted from the optical emitter based on the optical rotation of the light for use in determining a physiological characteristic of the tissue sample.

2. The optical pathlength measurement system of claim 1, wherein the first and second filters comprise first and second polarizers respectively.

3. The optical pathlength measurement system of claim 2, further comprising a modulator for modulating the light after it passes through the first polarizer.

4. The optical pathlength measurement system of claim 3, wherein the modulator is driven by a sinusoidal source for phase modulating an electric field of the light.

5. The optical pathlength measurement system of claim 3, wherein the modulator is a faraday rotator modulator.

6. The optical pathlength measurement system of claim 2, wherein the first polarizer comprises a polarization axis oriented at a reference angle.

7. The optical pathlength measurement system of claim 6, wherein the second polarizer comprises a polarization axis oriented orthogonally to the polarization axis of the first polarizer.

8. The optical pathlength measurement system of claim 7, wherein a polarization axis of the second polarizer is located at an angle of forty-five degrees from the reference angle.

9. The optical pathlength measurement system of claim 6, wherein the reference angle is zero degrees from the horizontal.

10. The optical pathlength-measurement system of claim 1, further comprising a photoelastic modulator for modulating the light after is passes through the tissue.

11. A method of determining an optical pathlength of a light after it passes through a tissue sample comprising:
    irradiating a beam of light;
    applying a first filter to the light;
    applying a field configured to optically rotate the light as it passes through a tissue sample;
    applying a second filter to the light;
    detecting the rotation of the light;
    calculating a pathlength based on the rotation of the light.

12. The method of claim 11, wherein the first and second filters comprise first and second polarizers respectively.

13. The method of claim 11, further comprising modulating the light before it passes through the tissue sample.

14. The method of claim 13, wherein modulating the light further comprises phase modulating the light.

15. The method of claim 14, wherein modulating the light further comprises modulating the light using a sinusoidal source.

16. The method of claim 11, further comprising modulating the light after it passes through the tissue sample.

17. The method of claim 16, further comprising photoelastically modulating the light.

18. An optical pathlength measurement system for determining a pathlength of a light source passing through a tissue sample comprising:
- means for emitting light of one or more wavelengths;
- means for filtering the light emitted from the multiple wavelength optical emitter;
- means for optically rotating the light as it passes through a tissue sample;
- a second means for filtering the light after it passes through the tissue sample;
- means for detecting the light after it passes through the second polarizer; and
- means for determining and outputting a pathlength of the light emitted from the multiple wavelength optical emitter based on the optical rotation of the polarized light for use in determining a physiological characteristic of the tissue sample.

* * * * *